United States Patent [19]

Fodor et al.

[11] Patent Number: 4,491,677

[45] Date of Patent: Jan. 1, 1985

[54] ISOMER SEPARATION

[75] Inventors: Lawrence M. Fodor; Ronald D. Knudsen, both of Bartlesville, Okla.

[73] Assignee: Phillips Petroleum Company, Bartlesville, Okla.

[21] Appl. No.: 510,856

[22] Filed: Jul. 5, 1983

[51] Int. Cl.$^3$ ............................................. C07C 37/84
[52] U.S. Cl. ..................................... 568/751; 568/750
[58] Field of Search ................................. 568/750, 751

[56] References Cited

U.S. PATENT DOCUMENTS 2,042,331  5/1936  Carswell ............................ 568/750
2,339,388  1/1945  Engel ................................. 568/750

Primary Examiner—Werren B. Lone
Attorney, Agent, or Firm—L. M. Lavin

[57] ABSTRACT

A process for the separation of isomeric cresols includes the step of crystallizing from a medium containing phenolic and solvent components.

9 Claims, No Drawings

ISOMER SEPARATION

BACKGROUND

Mixed cresols, i.e. mixtures containing isomeric methyl-substituted phenols, are obtainable from both natural and synthetic sources. Natural sources include coke, distillates, petroleum, tar sands, and shale oil. Synthetic sources include reactions involving benzene or derivatives thereof. One of the isomers present in mixed cresols, p-cresol, is useful in the preparation of many specialty chemicals. Among them is the antioxidant 2,6-ditertiary-butyl-p-cresol.

While o-cresol can be effectively removed from mixtures of cresol isomers, via conventional distillation techniques, the boiling points of m- and p-cresols are such that they cannot be easily separated by conventional distillation techniques. Accordingly, there is a need for a process by which m- and p-cresol isomers can be separated without complicated physical and/or chemical manipulation.

THE INVENTION

The invention deals with the separation of position isomers of aromatic compounds. In particular it has been discovered that high-purity p-cresol can be recovered from mixtures containing m- and p-cresols effectively employing a process which includes at least one recrystallization from organic solvent in the presence of one or more phenolic compounds.

In one embodiment a mixture of m- and p-cresol is separated by recrystallization from toluene in the presence of bisphenol A, with the optional inclusion of phenol. A 97% p-cresol/3% m-cresol mixture can be thus obtained from a 50/50 weight ratio mixture.

OBJECTS OF THE INVENTION

It is one object of the invention to provide a process for the preparation of cresol products having increased p-cresol content in a recrystallization in the presence of certain nonreactive media.

It is another object to provide a process for the recovery of high purity m- or p-cresols from mixtures containing them via crystallization and, optionally, distillation steps.

ADVANTAGES

The process of the invention offers several advantages over prior art techniques for separating mixtures of aromatic compounds. Heretofore, the separation of meta- and para-isomers of cresol called for butylation, distillation of the butylated mixture, and debutylation to recover separate isomers. The instant process avoids this time consuming and expensive sequence of chemical and physical operations.

The use of one or more recrystallization steps in the presence of specified crystallization or recrystallization media, followed by distillation or other conventional recovery operations, yields high purity p-cresols. Furthermore, since the media required for the one-time or sequential recrystallization(s) are relatively inexpensive, the overall cost is lower than the costs of other processes which require solvents and/or chemical reactions.

Other advantages and objects will become apparent from consideration of the following description.

DESCRIPTION OF THE INVENTION

Cresol Mixtures

The cresol mixtures which can be separated by the instant process are commercially available. They can be obtained via conventional techniques for the preparation of cresols, e.g., refinery waste streams, coal gasification byproducts and the sulfonation of toluene. Such reactions generally yield mixtures of meta- and para-isomers of cresol which are not easily separable by distillation.

Isomeric mixtures which are separated in accordance with the invention are typically 50/50 m- and p-cresols by constitution. It has been found that by using a series of crystallizations from appropriate media recoveries of about 5–40%, preferably about 19–30%, p-cresol are obtained in each crystallization step.

Phenolic Compounds

The phenolic compounds employed as components of the media from which p-cresol is crystallized and/or recrystallized in accordance with the invention conform to the general formula

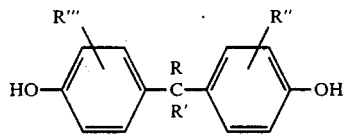

wherein R, R', R" and R''' are independently selected from H, and alkyl or cycloalkyl radicals having 1 to 6 carbon atoms. Such materials include but are not limited to:

bis-(4-hydroxyphenyl)methane
1,1-bis(4-hydroxyphenyl)ethane
2,2-bis(4-hydroxyphenyl)propane (Bisphenol A)
2,2-bis(4-hydroxyphenyl)butane
7,7-bis(4-hydroxyphenyl)tridecane
bis(4-hydroxphenyl)-bis(cyclohexyl)methane Bisphenol A is preferred. Mixtures of phenolic compounds can be employed.

The amount of phenolic compound employed depends upon the character of the cresol mixture to be separated. Generally, for a 50/50 isomer blend, the weight ratio of the phenolic compound to mixed cresols is about 5:1 to about 1:5 with ratios of about 2:1 to about 1:2 preferred.

Solvents

The other compound used in the crystallization media herein comprises one or more solvents. The solvents employed are inert substances whose miscibility with other organic substances renders them capable of dissolving cresols and phenolic compounds when warm.

Solvents employed herein include $C_3$ to $C_{15}$ hydrocarbons. Preferred solvents are aromatic and paraffinic compounds containing from about 5 to about 12 carbon atoms. Useful aromatic solvents include benzene, toluene, xylenes, and mixtures thereof. Useful paraffinic solvents are pentanes, methylcyclopentane, hexanes, octanes, dodecane, and the like and mixtures thereof. Mixtures of aromatic and non-aromatic solvents can be employed.

The weight ratio amounts of diluent or solvent employed to the cresol mixtures will generally be in weight ratios of about 50:1 to about 2:1, with the ratios of about 20:1 to about 10:1 preferred.

Procedure

The crystallization procedure employed is conventional. That is, the mixed cresol feed is contacted with phenolic compound(s) and solvent(s) in the crystallization media. If necessary, heat is applied to aid the solution process. Temperatures on the order of about 50° C. to about 100° C. are useful.

The resulting solution is permitted to stand, with optional temperature and/or pressure variation, e.g. cooling, so that crystals of the desired isomer are formed and precipitate out as a p-cresol-rich fraction. The crystal fraction is then recovered via conventional techniques, e.g. filtration. The liquid fraction may be recycled or treated to remove the m-cresol therefrom.

In a preferred embodiment, the crystal fraction is then dissolved in more phenolic compound/solvent media and recrystallized. Such recrystallization can be carried out several times, with one to five repetitions generally being effective to yield high-purity p-cresol.

As an analytical step, the crystals produced after any crystallization step can be silylated and subjected to gas-liquid chromatography to determine their constitution.

Conventional recovery techniques, such as distillation and the like, can be employed to fractionate the p-cresol-rich crystals, the m-cresol-rich liquor or both.

EXAMPLES

EXAMPLE I

This example illustrates the operability of the invention and describes the procedure used to separate m- and p-cresol from each other by recrystallization in the presence of Bisphenol A. To a flask was charged 2 grams of m-cresol, 2 grams of p-cresol, 2.5 grams Bisphenol A and 70 milliliters of toluene. The mixture was warmed on a steam bath until a homogeneous solution resulted. After standing overnight at ambient room temperature the crystals that precipitated were filtered, washed with about 30 milliliters of toluene, dried, and weighed (2.5 grams). The crystals were silylated by adding 10–20 milligrams of the crystals to 0.5 milliliters of pyridine and 0.5 milliliters of Regisil RC-1, bis(trimethylsilyl) trifluoroacetamide, from Regis Chem. Co. Separation of the silylated Bisphenol A, m-cresol, and p-cresol products was accomplished by using a Gas Liquid Chromatograph with an OV-101 capillary column (50 m×0.31 mm) programmed to hold at 100° C. for 2 minutes then increased at 16° C./minute to 250° C. In this way there was shown to be 2.01 grams Bisphenol A, 0.38 grams p-cresol and 0.10 gram m-cresol. The para-, meta-cresol weight ratio has now changed from 50:50 to 79:21.

Because of the small amount of m- and p-cresol separated by crystallization, a simulated mixture of the approximate concentration was prepared comprised of 2.5 grams Bisphenol A and a 75:25 p-, m-cresol mixture (3.0 grams p-cresol and 1.0 grams m-cresol). Toluene, 70 milliliters, was added and the mixture heated to dissolve the crystals. After standing overnight at ambient room temperature there was formed a crystalline product that upon washing with toluene and air drying weighed 3.15 grams. Repeating the silylation and analytical procedure herein described gave 2.5 grams Bisphenol A, 0.48 gram p-cresol, and 0.02 gram m-cresol. The cresol mixture, thus, contained 96% p-cresol and 4% m-cresol.

EXAMPLE II

This illustrates the separation of p- and m-cresol by recrystallization in the presence of Bisphenol A and phenol. The results show the presence of phenol does not significantly alter the cresol separation. The procedure described in Example I was repeated but using 2.5 grams of Bisphenol A and 2.5 grams of phenol along with 2 grams each of m- and p-cresol and 70 milliliters of toluene. These results from the two recrystallization steps are listed in Table I along with those from Example I for comparison. Both examples illustrate good separation of m- and p-cresol.

TABLE I

SEPARATION OF M-CRESOL/P-CRESOL MIXTURES BY RECRYSTALLIZATION

| Run No. | Recrystal- lization Step | Before Recrystallization in 70 mL Toluene, grams | | | | Recrystallized Solid Product[a], grams | | | |
|---|---|---|---|---|---|---|---|---|---|
| | | Bis-A[b] | Phenol | p-Cresol | m-Cresol | Bis-A[b] | Phenol | p-Cresol | m-Cresol |
| 1 | I | 2.5 | — | 2 | 2 | 2.01 | — | 0.38 (79%) | 0.10 (21%) |
| | II | 2.5 | — | 3.0 (75%) | 1.0 (25%) | 2.50 | — | 0.48 (96%) | 0.02 (4%) |
| 2 | I | 2.5 | 2.5 | 2 | 2 | 1.66 | 0.02 | 0.39 (75%) | 0.13 (25%) |
| | II | 2.5 | 2.5 | 3.0 (75%) | 1.0 (25%) | — | — | 0.64 (97%) | 0.02 (3%) |

[a]Cresols identified by GLC wherein products silylated with Regisil RC-1(bis(trimethylsilyl)trifluoroacetamide, Regis Chem. Co.
[b]Bisphenol A

EXAMPLE III

This example illustrates the separation of the m- and p-cresol mixture from Bisphenol A by distillation. The products obtained from Examples I and II illustrate the separation of m- and p-cresol. However, the amount of products separated were very small such that any subsequent separation of the cresols from Bisphenol A would be difficult. Therefore, larger quantities of recrystallized products were synthetically prepared to simulate the products after the first crystallization step. For example, a mixture of 10 grams of m-cresol, 30 grams of p-cresol, 25 grams of Bisphenol A was dissolved in 700 milliliters of hot toluene. After cooling overnight, the crystallized material was analyzed and found to contain 0.6 gram m-cresol, 10.2 grams p-cresol, and 20.6 grams of Bisphenol A. This example was the total of two runs which were repeated to accumulate product. The combined recrystallized products were subjected to distillation at 137° to 155° C./35 to 1 mm whereupon an overhead distillate fraction contained 0.58 gram m-cresol, and 9.06 grams of p-cresol. The kettle product contained 21.4 grams of Bisphenol A. These results are listed in Table II based on a single run and show two things: namely, that m- and p-cresol can be separated by crystallization in the presence of Bisphenol A and that, although m- and p-cresol cannot be separated by distillation, the mixture of cresols can be separated from Bisphenol A by distillation.

TABLE II

Separation of m-Cresol/p-Cresol Mixtures by Recrystallization and Distillation

| | Toluene | Components, grams[a] | | Bisphenol A |
| --- | --- | --- | --- | --- |
| | | m-Cresol | p-Cresol | |
| 1. Before Recrystallization | 700 mL | 10 (25%) | 30 (75%) | 25 |
| 2. After Recrystallization, solids | | 0.6 (5.6%) | 10.2 (94.4%) | 20.6 |
| 3. Distillation:B.P. 135–155° C./ 35—1 mm | | | | |
| a. Overhead Distillate | | 0.58 (6.0%) | 9.06 (94.0%) | 0 |
| b. Kettle Product | | — | — | 21.4 |

[a]Two batch runs were combined for recrystallization step.

Reasonable variations, such as those which would occur to skilled artisans, may be made herein without departing from the scope of the invention.

We claim:

1. A process for recovering high purity m- or p-cresol from a mixture containing them which comprises the steps of:

(1) contacting the mixture with a crystallization medium containing (a) a phenolic compound of the formula:

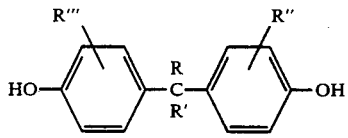

in which R, R', R", and R''' are independently selected from H and alkyl or cycloalkyl radicals having 1 to 6 carbon atoms, (b) and an inert solvent capable of dissolving said cresol mixture and said phenolic compound (2) cooling said mixture to produce a crystal fraction rich in p-cresol and a liquor rich in m-cresol, and (3) recovering the crystal fraction.

2. The process of claim 1 wherein the product of step (3) is recrystallized under the conditions used in steps (1) and (2).

3. The process of claim 2 wherein the solvent employed is selected from the group consisting of benzene, toluene, xylene, octane and mixtures thereof.

4. The process of claim 3 wherein the phenolic compound is bisphenol A.

5. The process of claim 4 wherein the solvent is toluene.

6. The process of claim 2 wherein p-cresol is separated from said crystal fraction by distillation.

7. The process of claim 5 wherein p-cresol is separated from said crystal fraction by distillation.

8. The process of claim 1 where said phenolic compound is bisphenol A.

9. The process of claim 2 wherein more than two recrystallization steps are used to recover p-cresol.

* * * * *